US011596304B2

(12) United States Patent
Dawson et al.

(10) Patent No.: US 11,596,304 B2
(45) Date of Patent: Mar. 7, 2023

(54) NEURAL PROBE INTERFACE SYSTEM AND METHOD (71) Applicant: University of Strathclyde, Glasgow (GB)

(72) Inventors: Martin David Dawson, Glasgow (GB); Keith Mathieson, Glasgow (GB); Gabor Varkonyi, Glasgow (GB); Jonathan McKendry, Glasgow (GB)

(73) Assignee: UNIVERSITY OF STRATHCLYDE, Glasgow (GB)

( * ) Notice: Subject to any disclaimer, the term of this patent is extended or adjusted under 35 U.S.C. 154(b) by 188 days.

(21) Appl. No.: 16/651,449

(22) PCT Filed: Aug. 22, 2018

(86) PCT No.: PCT/GB2018/052379
§ 371 (c)(1),
(2) Date: Mar. 27, 2020

(87) PCT Pub. No.: WO2019/063964
PCT Pub. Date: Apr. 4, 2019

(65) Prior Publication Data
US 2020/0281468 A1   Sep. 10, 2020

(30) Foreign Application Priority Data
Sep. 29, 2017   (GB) ...................... 1715910

(51) Int. Cl.
*H04B 10/114* (2013.01)
*A61B 5/00* (2006.01)
(Continued)

(52) U.S. Cl.
CPC .............. *A61B 5/0017* (2013.01); *A61B 5/24* (2021.01); *A61N 1/37217* (2013.01); *H04B 10/114* (2013.01); *H04L 7/0075* (2013.01)

(58) Field of Classification Search
CPC .... A61B 5/0017; A61B 5/24; A61N 1/37217; H04B 10/114; H04L 7/0075
See application file for complete search history.

(56) References Cited

U.S. PATENT DOCUMENTS 8,208,818 B2 * 6/2012 Sasai ...................... H04B 1/707
                                                      398/189
9,906,870 B2 * 2/2018 Shah ........................ H04R 1/42
(Continued)

FOREIGN PATENT DOCUMENTS

WO   WO-2010042750 A2 *  4/2010  ........... A61B 5/0031

OTHER PUBLICATIONS

Scharf et al. (Depth-specific optogenetic control in vivo with a scalable, high-density μLED neural probe: Robert Scharf, Tomomi Tsunematsu, Niall McAlinden1, Martin D. Dawson, Shuzo Sakata & Keith Mathieson, Jun. 23, 2016) (Year: 2016).*
(Continued)

*Primary Examiner* — Jai M Lee
(74) *Attorney, Agent, or Firm* — Dority & Manning, P.A.

(57) ABSTRACT

An interface or communications system for a neural probe, the interface or communications system comprising at least one probe interface, an optical communications interface and a processing system. The at least one probe interface is configured to interface with at least one neural probe so as to receive data collected by the probe. The processing system is configured to process the data from the at least one probe interface and provide the processed data to the optical communications interface. The optical communications interface is configured to communicate the processed data to a remote device, e.g. using optical wireless communications. The optical communications interface has the large bandwidth available that will allow the scaling up of recording
(Continued)

sites from the neural probe without resulting in undue size, weight and/or power consumption.

18 Claims, 6 Drawing Sheets

(51) Int. Cl.
*A61N 1/372* (2006.01)
*H04L 7/00* (2006.01)
*A61B 5/24* (2021.01)

(56) References Cited

U.S. PATENT DOCUMENTS

| | | | | |
|---|---|---|---|---|
| 10,433,754 | B2* | 10/2019 | Nurmikko | A61N 1/37217 |
| 2005/0216072 | A1* | 9/2005 | Mahadevan-Jansen | A61B 5/0048 600/89 |
| 2011/0024771 | A1* | 2/2011 | Hajj-Hassan | B82Y 15/00 257/84 |
| 2011/0087311 | A1* | 4/2011 | Zorzos | G02B 6/0008 607/89 |
| 2012/0116155 | A1* | 5/2012 | Trusty | H04B 10/1143 600/109 |
| 2013/0030274 | A1* | 1/2013 | Jamieson | A61B 5/6848 600/377 |
| 2013/0079615 | A1* | 3/2013 | Yoon | A61B 5/24 600/377 |
| 2014/0142664 | A1* | 5/2014 | Roukes | A61N 5/0622 607/88 |
| 2014/0371564 | A1* | 12/2014 | Anikeeva | A61N 5/0622 600/377 |
| 2015/0148688 | A1* | 5/2015 | Cho | A61B 5/0084 600/478 |
| 2015/0338248 | A1* | 11/2015 | Kalelkar | G01N 11/16 73/862.624 |
| 2016/0367836 | A1* | 12/2016 | Kampasi | A61N 5/0622 |
| 2019/0091484 | A1* | 3/2019 | Lai | A61N 5/0601 |
| 2020/0281468 | A1* | 9/2020 | Dawson | A61B 5/0017 |
| 2020/0298005 | A1* | 9/2020 | Howard | A61B 5/686 |
| 2021/0085996 | A1* | 3/2021 | Cho | A61B 5/4064 |

OTHER PUBLICATIONS

Várkonyi et al. (Data Transmission for High-Bandwidth Neural Interfacing Using Visible Light Communication: Gábor Várkonyi, Jonathan J. D. McKendry, Niall McAlinden, Martin D. Dawson and Keith, 2016). (Year: 2016).*

PCT International Written Opinion for corresponding PCT Application No. PCT/GB2018/052379, dated Jan. 22, 2019—7 pages.

Várkonyi et al. "Data transmission for high-bandwidth neural interfacing using visible light communication," 2016 IEEE Photonics Conference (IPC), Waikoloa, HI, 2016, pp. 41-42.

McAlinden et al., "Optogenetic activation of neocortical neurons in vivo with a sapphire-based micro-scale LED probe," Frontiers in Neural Circuits, May 29, 2015, vol. 9, Article 25—8 pages.

McAlinden et al., "Thermal and optical characterization of micro-LED probes for in vivo optogenetic neural stimulation," Optics Letters, Mar. 15, 2013, vol. 38, No. 6—3 pages.

Kim et al., "Injectable, Cellular-Scale Optoelectronics with Applications for Wireless Optogenetics," Science, Apr. 12, 2013, vol. 340, Issue 6129, pp. 211-216.

Scharf et al. "A compact integrated device for spatially selective optogenetic neural stimulation based on the Utah Optrode Array," Progress in Biomedical Optics and Imaging, SPIE—International Society for Optical Engineering, Optogenetics and Optical Manipulation, Feb. 14, 2018—9 pages.

Scharf et al. "Depth-specific optogenetic control in vivo with a scalable, high-density μLED neural probe," *Scientific Reports*, Vo. 6, No. 1, Jun. 23, 2016—10 pages.

PCT International Preliminary Report on Patentability for corresponding PCT Application No. PCT/GB2018/052379, dated Mar. 31, 2020, 9 pages.

European Office Action for corresponding European Application No. 18799586.5, dated Sep. 14, 2022, 9 pages.

Rhee et al., "Optical orthogonal frequency division multiplexed transmission using all-optical discrete Fourier transform", Laser & Photonics Reviews, vol. 7, No. 4, 2013, pp. 539-553.

* cited by examiner

NEURAL PROBE INTERFACE SYSTEM AND METHOD

PRIORITY CLAIM

This application is based upon and claims the right of priority under 35 U.S.C. § 371 to International Application No. PCT/GB2018/052379 filed on Aug. 22, 2018, which claims priority to GB Application Serial No. 1715910.4 filed on Sep. 29, 2017, each of which is incorporated by reference herein in its entirety.

FIELD

The present disclosure relates to an interface or communications system for a neural probe, wherein the neural probe is usable for interfacing with a brain or other neural system.

BACKGROUND

Neural probes have long been used to interface with the brain of a subject, such as a human, mouse, monkey or other animal. Such probes are particularly useful in the study of the brain and can also be used in a range of uses in non-scientific applications that require an interface to the brain, the nervous system or other neural structures of the subjects.

It is desirable to allow the subject close to free movement, avoid discomfort for the subject and to generally not interfere with the subject's response. In the scientific field, such probes are often used with small animals, such as mice, where such considerations are even more acute. As such, neural probes and associated ancillary systems generally need to be minimally invasive, small and light weight and at the same time communicate large amounts of data. Powering of such devices can also be an issue.

The neural probes may comprise one or more probes for measuring activity or response of parts of the brain, nervous system or other neurological structure and may comprise one or more stimulators, for stimulating selected parts of the brain, nervous system or other neurological structure. The stimulators and/or probes could be electrical and/or optical and examples of suitable probes are those provided by NeuroNexus of Ann Arbor, Mich. This facilitates a 2-way exchange of data with neural circuits providing control and interrogation of neural signalling.

There is a general trend towards using larger numbers of probes (1000's or 10,000's) in order to record electrical (e.g. voltage) potentials from larger numbers of neurons. The field has been enhanced by the advent of optogenetics allowing light activation of specific cells. These trends increase the data transmission requirements, which often conflict with the desire for the probe and ancillary components to be small, minimally invasive, low power and light weight. This may result in devices that are too heavy, cumbersome or uncomfortable, particularly for small animals such as mice. This could also lead to limited data transmission bandwidth, e.g. reduced channel count, compression of data which can lead to loss of information or increased processing burden and/or latency, low analogue to digital resolution, or short recording times. These compromises may also lead to shorter operational life or range.

At least one example of the present disclosure seeks to address at least one problem in the prior art, which may include those identified above.

SUMMARY

Various aspects of the present disclosure are defined in the independent claims. Some preferred features are defined in the dependent claims.

According to a first aspect of the present disclosure there is provided an interface or communications system for a neural probe, the interface or communications system comprising:

at least one probe interface configured to interface with at least one neural probe so as to receive data collected by the probe; and an optical communications interface configured to communicate the data or data derived therefrom (e.g. processed data) with a device, such as a remote device.

The communications system may comprise a processing system. The processing system may be configured to process the data from the at least one probe interface and provide the processed data to the optical communications interface. The processing system may be configured to process the data from, and/or provide data to, the at least one probe interface and/or the optical communications interface. The processing system may be coupled to and/or between the at least one probe interface and the optical communications interface. The processing system may be configured to convert the data received from the neural probe into data for transmission using the optical communications interface, which may comprise converting the data from one format into a different format. The derived data may be the converted data. The processing system may be configured to provide the converted data to the optical communications interface.

The optical communications interface may be or comprise or be comprised in a wireless or free space communications system. The optical communications interface may be or comprise or be comprised in an optical wireless communications (OWC) interface. The optical communications interface may be configured to communicate without using optical fibres. The optical communications interface may comprise at least one optical communications light source, which may be or comprise an LED, or an RCLED (for example those available from Firecomms) and/or the like. The at least one optical communications light source may be or comprise a first type of light source, e.g. an LED, with a characteristic output wavelength, power, luminance, response time, physical size, number of light sources, and/or the like.

The processing system may be configured to control or operate the at least one optical communications light source in order to encode the data and/or the converted or derived data in the light emitted from the at least one optical communications light source.

The device may be a remote device, such as an interrogator for interrogating the probe e.g. via the communications system. The device, e.g. the interrogator, may be or comprise or be comprised in a reading device for receiving data from the at least one neural probe via the communications system. The device may be or comprise or be comprised in a control system for controlling and/or providing data or instructions to the at least one probe, e.g. via the communications system. The communications system may be a two-way communications system (which may allow both control and interrogation of the neural tissue) or alternatively a one-way communications system.

The optical communications interface may comprise a reference and/or clock communications module. The reference and/or clock communications module may comprise at least one reference and/or light source, which may be an LED, and/or the like. The reference or clock communications module may be configured to communicate a clock or reference signal from the communications system or interface, which may be provided by optical communications such as optical wireless communications. The reference or clock communications module may be configured to transmit clock data or other data required for off-board synchronization. The at least one reference and/or light source may be or comprise a second type of light source, which may be a different type of light source to the at least one optical communications light source, e.g. having a different characteristic output wavelength, power, luminance, response time, physical size, number of light sources, and/or the like. The optical signals emitted by the at least one reference and/or light source may be orthogonal to and/or of a different frequency or wavelength to, or otherwise arranged so as not to interfere with, those emitted by the at least one optical communications light source.

The reference or clock signal may be received by the reference and/or clock communications module from the processing system. The processing system may be configured to control the at least one reference and/or clock light source in order to encode the reference or clock signal in the light emitted from the reference and/or clock light source.

The optical communications interface may be configured to communicate a plurality of different data streams, e.g. using the at least one optical communications light source. The optical communication interface may be configured to coalesce the plurality of different data streams into a single or combined data or communications stream. At least one or more of the different data streams may comprise or encode the data or the data derived therefrom (e.g. the processed data), which may be communicated to the device, e.g. the remote device. At least one of the different data streams may comprise the reference or clock signal. The reference or clock signal may be provided in a different data stream to the data or data derived therefrom. The data stream comprising the reference or clock signal may be coalesced with the different data stream comprising the data or data derived therefrom into the same single or combined data or communications stream. In this way, only a single LED may be required for data transmission, as opposed to a separate LEDs for the clock signal and data. One or more or each of the different data streams may employ different encoding techniques to one or more or each other different data stream. One or more or each of the data streams may be encoded using Manchester encoding or other forms of data multiplexing, such as OFDM. The plurality of different data streams may be separated or separable from the single or combined data or communications stream at the receiving end and/or at the device, e.g. with either dedicated hardware in real-time or by post-processing using software.

The at least one probe interface for interfacing with at least one neural probe may comprise a pin connector, a socket connector, high density interconnect technology, wire bonding, and/or the like, which may compliment a corresponding connector on the at least one neural probe. The at least one probe interface may be or comprise at least one electrical connector for communicating, receiving and/or providing electrical signals to and/or from the at least one neural probe. The at least one probe interface may be or comprise at least one optical connector for communicating, providing and/or receiving optical signals to and/or from the at least one neural probe. As an example, the at least one probe interface may be or comprise an Omnetics connector, such as the A79027-001 connector.

The at least one probe interface may be separate to, and/or spaced apart from, the optical communication interface. The at least one probe interface may be provided on an opposite side of the communications system to the optical communications interface. The at least one probe interface may be provided on a side of the communications system that faces the subject, in use. The optical communication interface may be provided on any side of the communications system apart from the side that faces the subject, in use, e.g. the optical communication interface may be provided on a side of the communications system that is opposite the side that faces the subject, in use.

The processing system may comprise an analogue to digital converter (ADC) and/or a digital to light converter. The processing system may comprise an amplifier. The amplifier and the ADC may be integrated, e.g. into a single, combined and/or unitary unit. The amplifier and/or ADC may be provided in a first processing module, which may be or comprise a first circuit or circuit board and/or semiconductor component/device. The at least one neural probe interface may be comprised in or provided on the first processing module or circuit or circuit board and/or semiconductor component/device. The at least one neural probe interface may be coupled or electrically connected to the ADC, the amplifier or the integrated amplifier/ADC. The amplifier and/or ADC or the integrated amplifier/ADC may be coupled to one or more registers, e.g. for temporarily storing data received from the at least one neural probe. The registers may be provided on the first processing module or first circuit or circuit board and/or semiconductor component/device.

The processing system may comprise at least one controller or processor such as a central processing unit (CPU) and/or a microcontrol unit (MCU). The controller or processor may optionally be comprised in a second processing module, which may be or comprise a second circuit or circuit board and/or semiconductor component/device. The optical communications interface may be comprised in the second processing module or circuit or circuit board and/or semiconductor component/device. The optical communications interface may be coupled or electrically connected to the at least one controller or processor.

The first and/or second circuit boards may be flexible or bendable circuit boards, e.g. comprising or provided on a flexible or bendable base or board, which may be polymeric.

The communications interface or system may be, comprise or be comprised in a multilevel or layered arrangement, e.g. comprising different circuits or circuit boards and/or semiconductor component/device on different levels. For example, the first processing module or circuit or circuit board and/or semiconductor component/device may be provided on a first layer or level of the communications system, and the second processing module or circuit or circuit board and/or semiconductor component/device may be provided on a second layer or level of the communications system, which may be different to the first layer. The first and second processing modules or circuits or circuit boards and/or semiconductor component/device may be stacked or layered, e.g. one on top of the other or overlapping or vertically stacked directly overlapping or on top of each other. In this way, the communications system may be made more compact and/or may operate faster and/or with less losses.

The second processing module or circuit or circuit board and/or semiconductor component/device (e.g. the at least one processor or controller) may be a master and the first processing module or circuit or circuit board and/or semiconductor component/device (e.g. the ADC and/or amplifier) may be a slave, e.g. to the second processing module or circuit or circuit board and/or semiconductor component/device. The second processing module or circuit and/or semiconductor component/device, e.g. the at least one controller or processor, may be configured to control the first processing module or circuit and/or semiconductor component/device (e.g. the ADC and/or amplifier), e.g. to set up the registers, perform calibration, to control the analogue to digital conversion, to provide clock signals, chip select signals, other signals for clocking or synchronization and/or the like.

The optical communications interface and/or at least the at least one optical communications light source may be coupled to an output, such as a digital output, of the processing system. The output may be or comprise or be comprised in a master in slave out (MISO) output. The optical communications interface and/or the at least one optical communications light source may be coupled to the output of the processing system via a resistive element, which may comprise one or more resistors. The resistive element may be configured to cap or limit the current flowing to the at least one optical communications light source. This overall arrangement may be more power efficient and/or may prevent damage to one or more components.

The interface or communications system may comprise a power source or power storage, which may comprise an electrochemical power storage, such as a battery or cell, e.g. a lithium or lithium-polymer or lithium ion battery or cell, or an air cell, such as a zinc-air or lithium-air cell. The power storage may be interfaced and charged using regular pin connectors to allow the complete disconnection of it from the system or may be configured to be inductively or wirelessly charged and/or the like. The interface or communications system may comprise a physical switch to physically and/or electrically disconnect the battery from the rest of the system. The power source or power storage may be provided on or in the second processing module or circuit or circuit board. The communications system may comprise a voltage controller for regulating or controlling the power provided by the power source or power storage to the other components of the communications system, e.g. to the ADC, the amplifier, the processor or controller, the optical communications interface, and/or the at least one probe interface, e.g. for powering and/or providing signals, such as stimulating signals, to the probe. The power source may comprise an inductive coupling power supply, or a radio frequency power supply or a kinetic or perpetual power supply or some other form of wireless power supply system.

The interface or communications system may comprise a receiver, e.g. for receiving commands for controlling one or more or each of the components of the communications system and/or the at least one neural probe and/or other data such as stimulation data for provision by the one or more stimulators. The receiver may be configured to receive the commands and/or data from a controller, which may be or may be comprised in the device used to interrogate the interface or communications system. The receiver may be or comprise, e.g. an infra-red (IR) receiver, a Bluetooth or Wi-Fi receiver, an optical wireless communications (Li-FI) receiver, and/or the like. The receiver may be configured to communicate with a mobile device, such as a smartphone and the receiver may be configured to receive data from the mobile device. The smartphone may use an app, which may implement a user interface, e.g. to allow a user of the device to select or provide control commands or data.

The probe may be comprised of a probe comprising of one or more electrical connections, which may be supported on a supporting structure, such as an elongated supporting structure that may be thin or needle like to allow for easy insertion and/or minimising tissue damage. Examples of such probes are those provided by NeuroNexus, Ann Arbor, Mich. However, the probe need not comprise such a structure and may simply comprise, in its simplest form, an electrical connection, wire or other electrical contact or connectors suitable for insertion into a body and for collecting electrical neural or brain activity, or an array of such electrical contacts or connectors. Furthermore, the probe may be used in an in-vitro configuration.

The neural probe may be or comprise or be comprised in an optical probe, such as a probe for optogenetic stimulation. The neural probe may comprise a probe that comprises, is coupled to or is configured to receive light from a light source, such as an LED. At least one or each of the neural probes may be or comprise an integrated probe, which may comprise both at least one stimulator and at least one probe. The light source used to provide light to the at least one neural probe may be, or may share at least some ancillary components with the optical communications interface. For example, both the light source used to provide light to the at least one neural probe and the optical communications interface may share one or more of: the stimulator circuitry, ADC, the amplifier, the processor or controller, the voltage controller, the matching element, resistive element and/or the like.

The interface or communications system may be locatable or be configured to be located outwith a body. For example, the interface or communications system may be mounted or mountable to a portion of the probe that extends from the body, in use.

A transfer printing technique, such as soft-stamp based micro-transfer printing, may be used to integrate one or more or each of the light sources with the one or more of the circuit boards and/or the neural probe and/or the processing system and/or the amplifier, integrated amplifier/ADC and/or amplifier circuitry. This may allow the devices to be further miniaturized and/or enhance functionality. The application of the transfer printing technique to neural probe development may allow miniaturisation on a scale permitting the optical communications platform to be integrated on to the neural probe that could include the amplification circuitry (e.g. on CMOS probes). Furthermore, it may open up the use of micro-LEDs (LEDs of less than 100 microns diameter/side) integrated with the system, which can be switched faster, allowing large data rates that extend out to 10 s-100 Gb/s.

According to a second aspect of the present disclosure is a neural probe system comprising:
  at least one neural probe; and
  an optical communications interface for communicating the data to and/or from the at least one neural probe with a device.

The neural probe system may comprise a processing system for processing data from, and/or for providing to, the at least one neural probe and/or the optical communications interface. The processing system may be coupled to and/or between the at least one neural probe and/or the optical communications interface.

The optical communications interface may be or comprise an optical wireless communications (OWC) and/or freespace optical communications interface.

The at least one neural probe may be permanently coupled or connected to the optical communications interface and/or the processing system, or may be removably connected, e.g. via at least one probe interface.

The probe may be or comprise a probe comprising one or more electrical connections, which may be supported on a supporting structure, such as an elongate supporting structure that may be thin or needle like to allow for easy insertion and/or minimising tissue damage. Examples of such probes are those provided by NeuroNexus, Ann Arbor, Mich. However, the probe need not comprise such structure and may simply comprise, in its simplest form, an electrical connection, wire or other electrical contact or connector suitable for inserting into a body and for collecting electrical neural or brain activity, or an array of such electrical contacts or connectors.

The neural probe system may comprise at least one feature described above in relation to the first aspect of the disclosure, with the neural probe optionally removably or permanently coupled via the probe interface.

According to a third aspect of the present invention is a method of communicating data from a neural probe, the method comprising receiving data from a neural probe at the communication system or interface of the first aspect of the disclosure and transmitting the data via optical wireless communications using the optical communications interface of the communications system to a device, such as a remote device According to a fourth aspect of the present invention is an assembly comprising a device comprising an interrogator, and either a communications system according to the first aspect and a neural probe or a neural probe system according to the second aspect, wherein the interrogator is configured to receive data collected using the neural probe from the communications system or the neural probe system.

According to a fifth aspect of the present invention is a computer program or computer program product configured such that when run on a processing system causes the processing system to implement the method of the fourth aspect. The computer program or computer program product may be provided on a tangible, non-transient carrier medium.

According to a sixth aspect of the present invention is a method of producing an interface or communications system for a neural probe, such as an interface or communications system for a neural probe of the first aspect, the method comprising using a transfer printing technique to integrate one or more or each of the light sources with the one or more of the circuit boards and/or the neural probe and/or the processing system and/or the amplifier, integrated amplifier/ADC and/or amplifier circuitry.

It should be understood that the individual features and/or combinations of features defined above in accordance with any aspect of the present invention or below in relation to any specific embodiment of the invention may be utilised, either separately and individually, alone or in combination with any other defined feature, in any other aspect or embodiment of the invention.

Furthermore, the present invention is intended to cover apparatus configured to perform any feature described herein in relation to a method and/or a method of using or producing, using or manufacturing any apparatus feature described herein.

BRIEF DESCRIPTION OF THE DRAWINGS

Various aspects of the disclosure will now be described by way of example only and with reference to the accompanying drawings, of which.

DETAILED DESCRIPTION OF THE DRAWINGS

Described herein is a light weight, compact and unobtrusive interface or communications system that allows a neural probe to be interrogated by a remote interrogating device, which could optionally be a smartphone or tablet, a computer or a custom device, e.g. utilising FPGAs or the like. In particular, the interface or communications system receives data carrying signals from the neural probe, converts the data carrying signals into a format for onward transmission and then communicates the data using optical wireless communications (OWC). The interface or communications system advantageously comprises a receiver for receiving control commands and operating data such as stimulation schemes for controlling the interface or communications system and/or the neural probe.

FIGS. 1 to 6 show a communications system 5 in the form of a multi-level PCB, having a first circuit board 10 and a second circuit board 15 arranged in a stacked arrangement and electrically connected so as to pass data signals and power. The first and second circuit boards 10, 15 may beneficially be flexible circuit boards, e.g. with the components provided on a flexible or deformable substrate, which may improve comfort, but this need not necessarily be the case. Although the embodiment of FIGS. 1 to 6 comprises first and second circuit boards 10, 15, in other embodiments the components provided on the first and second circuit boards 10, 15 could instead by integrated into a single circuit board or in a single semiconductor device or two or more respective semiconductor devices.

Figure 1:
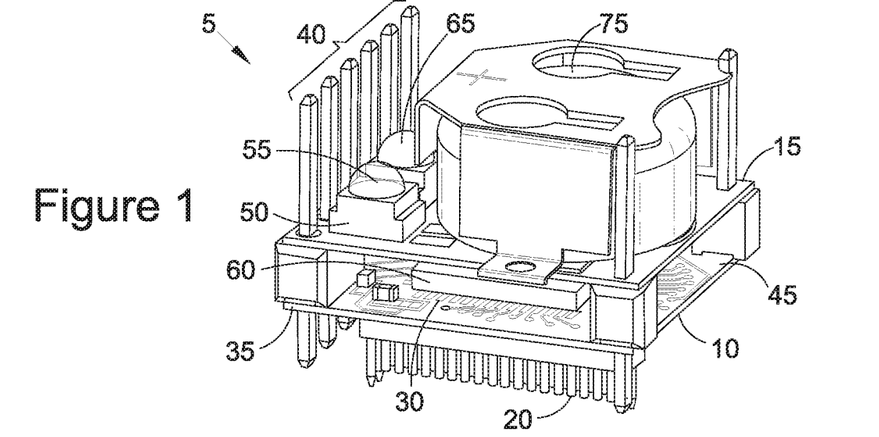
FIG. 1 is a perspective view of a communications system for a neural probe.
Figure 2:
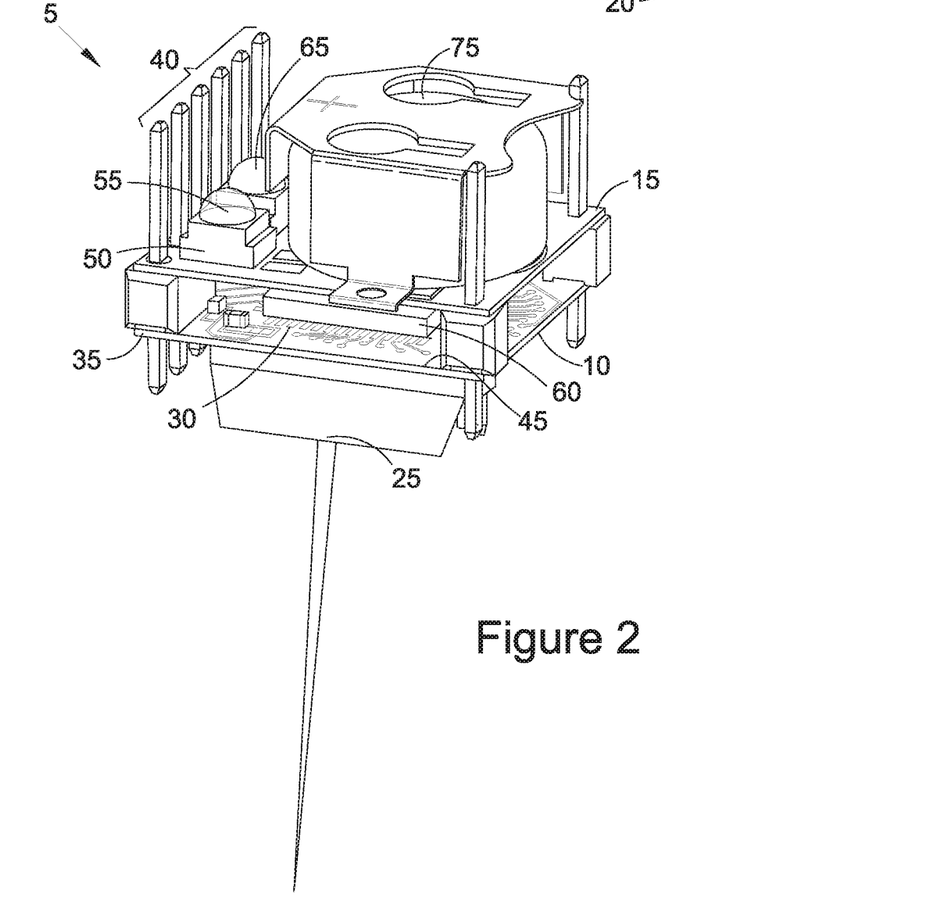
FIG. 2 is a perspective view of the communications system of FIG. 1 with the neural probe mounted.
Figure 3:
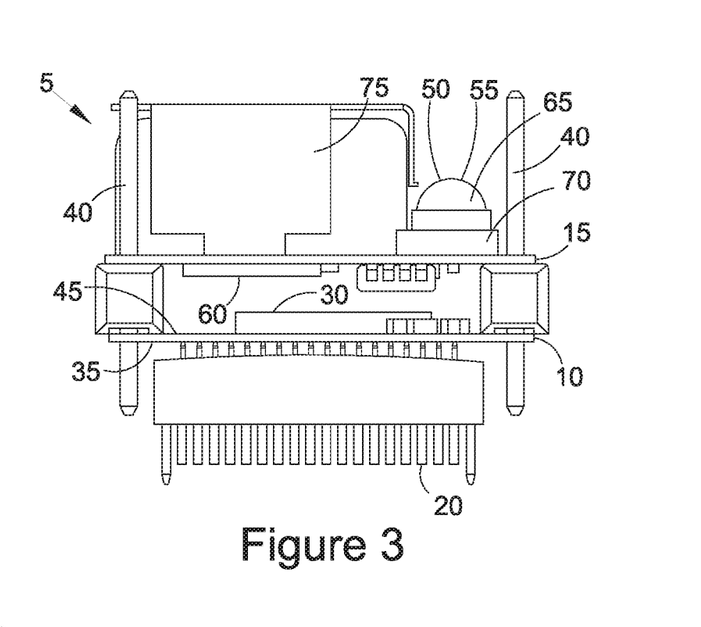
FIG. 3 is a side profile view of the communications system of FIG. 1.
Figure 4:
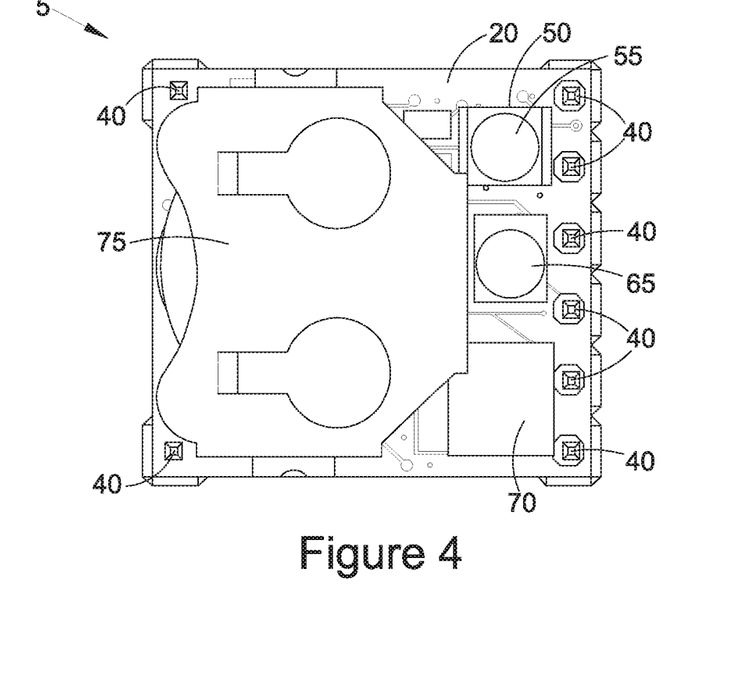
FIG. 4 is a top planar view from above the communications system of FIG. 1.

The first circuit board 10 comprises a probe interface 20 for interfacing with at least one neural probe 25 (see FIG. 2). In this example, the probe interface 20 comprises multiple pins. One example of a suitable probe interface 20 is an Omnetics A79027-001 connector. The neural probe 25 can take any suitable form, and can comprise both one or more stimulators for providing stimulations and one or more probes for measuring responses in the brain, neural structure or other structure of the nervous system, such as (but not limited to) responses to the stimulations provided by the at least one stimulator. Examples of suitable probes include those produced by NeuroNexus, Ann Arbor, Mich., but it will be appreciated that other suitable probes are available. The stimulator(s) and/or probe(s) may comprise electrical and/or optical stimulator(s) and/or probe(s). In the case that optical stimulator(s) and/or probe(s) are used, the probe 25 or probe interface 20 comprises optical to electrical convertors, such as photodiodes and/or the like. The probe 25 comprises a corresponding female/socket interface for receiving the pins of the probe interface 20 to thereby permit collection of data collected by the probe 25, e.g. by making electrical connections.

Figure 5:
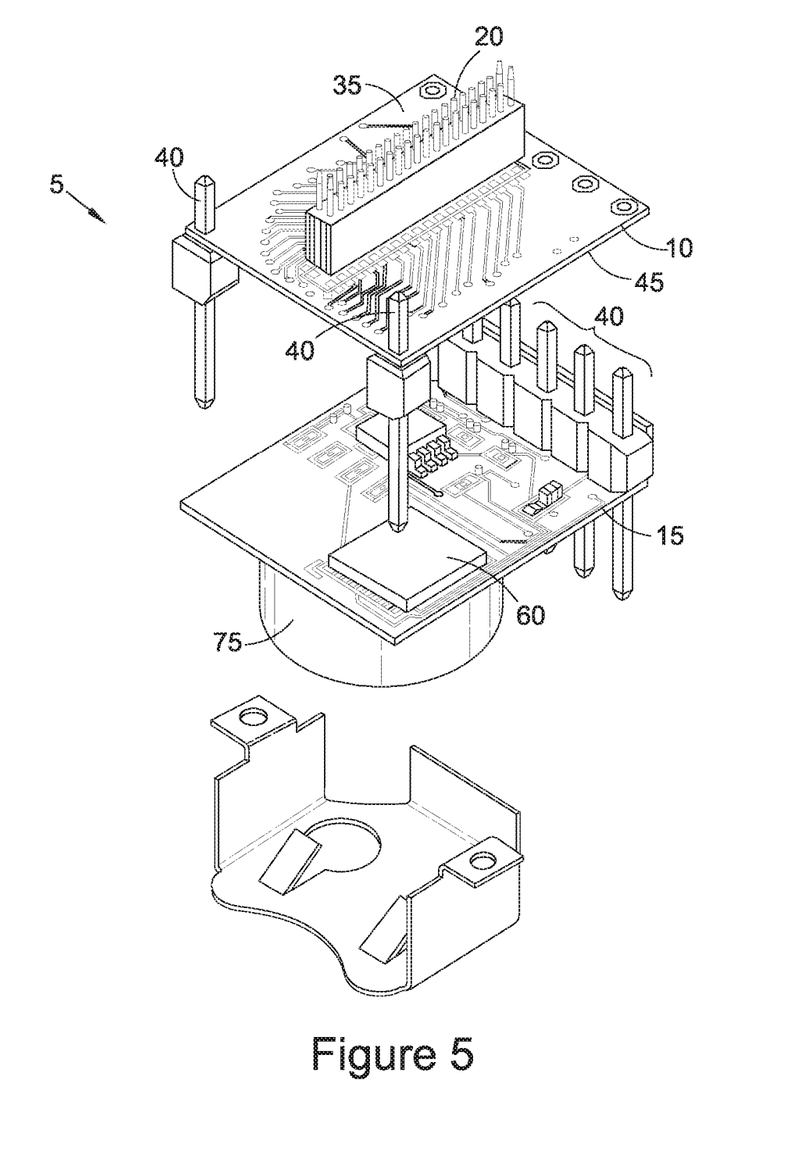
FIG. 5 is an exploded perspective bottom view of the communications system of FIG. 1.
Figure 6:
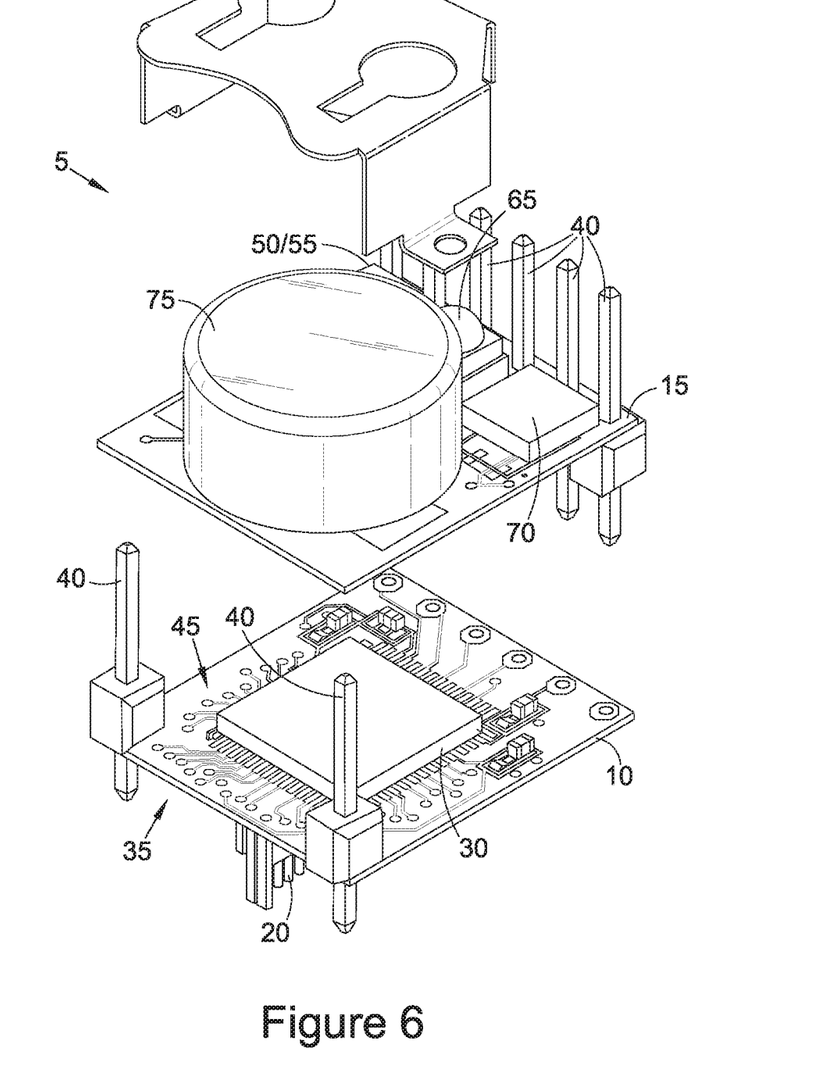
FIG. 6 is an exploded perspective top view of the communications system of FIG. 1.

The first circuit board 10 further comprises a signal convertor 30 in the form of an integrated analogue to digital converter (ADC) and amplifier. One example of a suitable example of a signal convertor 30 is an Intan 2132 16 bit amplifying analogue to digital converter, but it would be appreciated that other suitable signal convertors 30 could be used. The probe interface 20 is mounted on a first (outwardly facing) surface 35 of the first circuit board 10, whilst the signal convertor 30 and a plurality of inter-board circuit connectors 40 are provided on a second (inwardly facing) surface 45 of the first circuit board 10 that is opposite to the first (outwardly facing) surface 40. The second (inwardly facing) surface 45 of the first circuit board 10 faces the second circuit board 15. The inter-board circuit connectors 40 electrically connect with corresponding connectors (not shown) to provide power and data communications between the stacked first and second circuit boards 10, 15.

In particular, the inter-board circuit connectors 40 in the form of elongate pins are provided on at least one side edge of one or both of the first and second circuit boards 10, 15 and receiving sockets for receiving the pins of the other circuit board 10, 15 are provided on another (e.g. opposite) side edge of the respective first and/or second circuit boards 10, 15. In this way, the first and second circuit boards 10, 15 can be connected together in a stacked arrangement, with inter-circuit board connectors 40 from one or both of the first and second circuit boards 10, 15 fitting into corresponding sockets on the other circuit board 10, 15 on at least two side edges (e.g. opposite side edges) so as to form the stacked multi-layer circuit board 10, 15 arrangement.

An optical communications interface 50 for communicating with devices external to the communications system 5 is comprised in the second circuit board 15. The optical communications interface 50 in this example is an optical wireless communications system configured to encode a digitized version of the data collected using the neural probe 25 into optical signals and transmit the data through freespace to a remote optical receiver on an interrogating device (not shown). In particular, the optical communications interface 50 comprises a data communications light source 55, in this example in the form of an LED. As only one possible example, the data communications light source 55 is a Kingbright APETD3528SEC/J3-PRV LED, although it will be appreciated that a wide range of alternative LED or other light source types could be used instead. The light emitted by the light source can be beneficially configured to emit visible light but may optionally be configured to emit invisible (e.g. infra-red IR) signals. The light may be of a specific wavelength or band of wavelengths.

The second circuit board 15 further comprises a processing system in the form of a microcontroller 60 for processing data from the neural probe 25 received via the probe interface 20, the signal convertor 30, and the inter-board connectors 40. The microcontroller 60 is coupled to the optical communications interface 50 so as to be able to encode and provide the digitized data from the neural probe to the optical communications interface 50 for transmission "off-board" to a remote interrogating device. The optical communications interface 50 further comprises an impedance module 62a for impedance matching between the microcontroller 60 and the data communications light source 55 and for limiting a maximum current to the optical communications light source 55 in order to save power.

The data may be encoded in a suitable form for optical wireless communication, for example, by applying OFDM, on-off keying (OOK), M-QAM, and/or any other suitable optical data signal modulation technique. The light emitted by the data communications light source 55 is modulated under the control of the microcontroller so as to transmit an optical signal that encodes the data.

Figure 8:
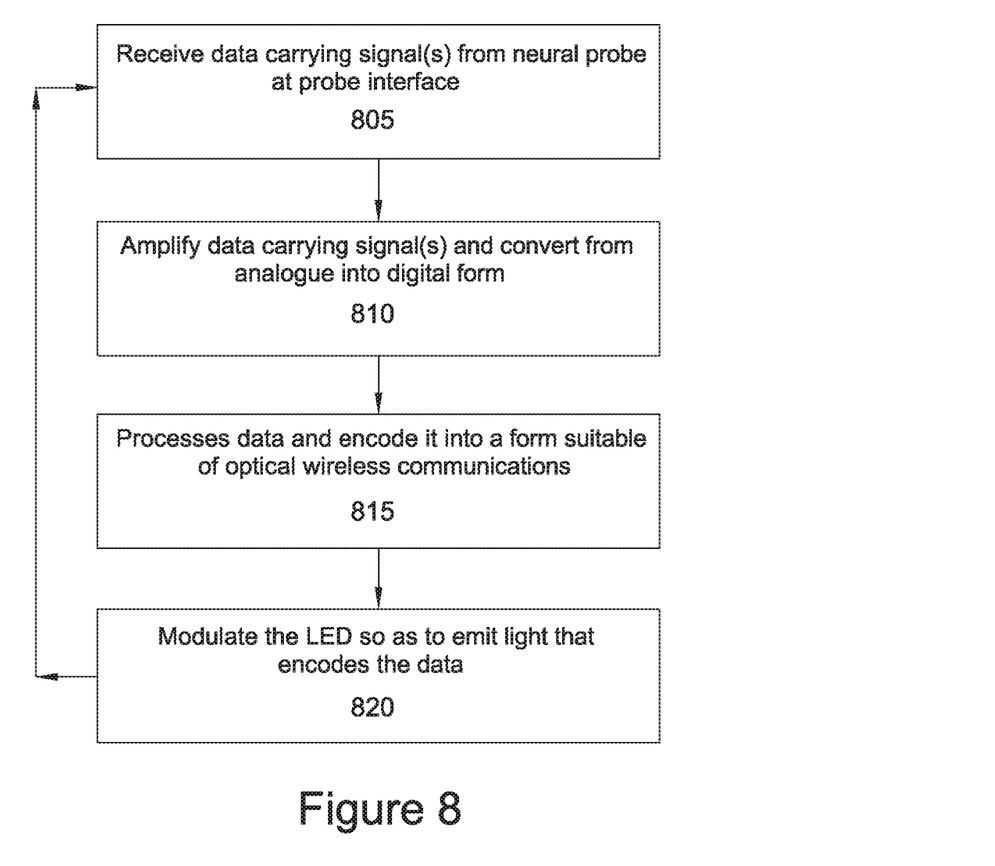
FIG. 8 is a flowchart showing a method of operating the communications system of FIG. 1.

In this way, as shown in FIG. 8, data collected by the neural probe 25 is received at the probe interface 20. The analogue data carrying signal from the probe is amplified and converted from analogue into digital form by the signal convertor 30 before being transferred between the first and second circuit boards 10, 15 via the inter-board connectors 40 to the data communications light source 55. The microcontroller 60 could also process the digitized neural probe data if further encoding is needed to enhance the optical wireless communications before modulating the data communications light source 55 so as to emit an optical signal that encodes the digitized neural probe data. The optical signal that encodes the digitized neural probe data can be received by a suitable optical receiver on a remote interrogating device (not shown).

A clock LED 65 is provided on the second circuit board 15 and transmits a clock signal from the signal convertor 30 using optical wireless communications to allow for off-board synchronisation at the interrogating device. Although an LED is beneficially used to optically transmit the clock signal, other light sources could be used instead. The clock LED 65 may be configured to emit visible light or non-visible light (e.g. IR). The interrogating device is configured to receive data signals from both the data communications light source 55 and the clock LED 65, e.g. respectively using a pair of optical detectors such as photodiodes or photomultipliers. The clock LED is of a different type to the data communications light source 55. In one particular example, the clock LED is an Avago HLMP-Q156 or an IR LED, but it will be appreciated that other suitable LEDs could be used. The data communications light source 55 and the clock LED 65 are configured such that the data carrying optical signals produced by them are orthogonal so as to be easily separable and individually recoverable. For example, each light source 55, 65 could be configured to transmit at a different wavelength or in non-overlapping wavelength ranges or bands. In other embodiments, this clock signal could be encoded in the data stream arising from data communications light source 55, by using a suitable data communications protocol such as, but not limited to, Manchester encoding. This could reduce power consumption and size further.

Figure 7:
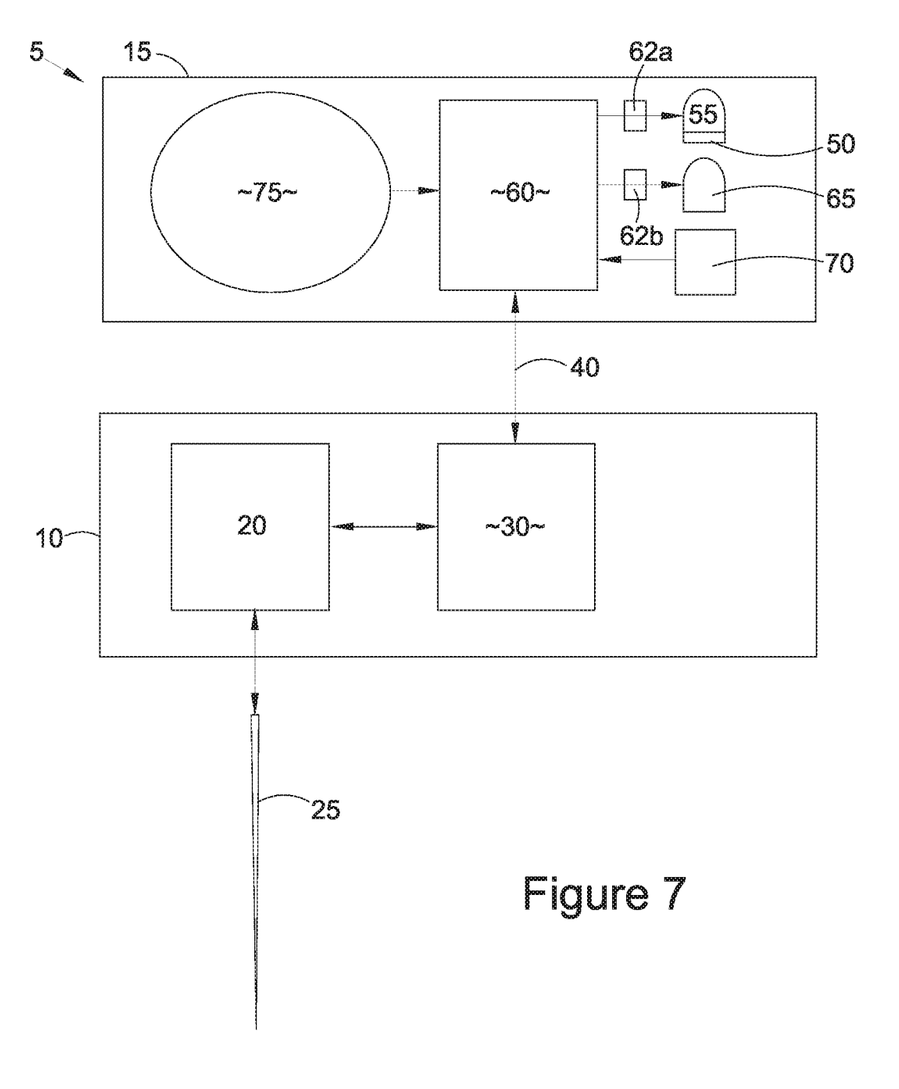
FIG. 7 is a schematic diagram of the communications system of FIG. 1.

The microcontroller 60 is also configured to control the signal convertor 30, for example, by supplying any required signals to the signal convertor 30, such as commands to set up registers of the signal convertor 30 upon initialization, calibrating the probe 25 or communications system 5, and for carrying out analogue to digital conversion of the probe data. The microcontroller 60 also sends chip select (CS) and the clock (e.g. serial data clock SCLK) to the signal convertor 30 so that the probe 25, communications system 5 and/or interrogator device can be synchronized.

The communications system 5 is also provided with a receiver 70, which in this example is beneficially an infrared (IR) receiver but could be some other form of wireless receiver, such as a Bluetooth, optical wireless communications or WI-FI receiver, and/or the like. The receiver 70 is coupled to the microcontroller 60 and allows the communications system 5 to receive commands from a control device, which may be the same device as the interrogator device.

The interrogator and/or control device could be, for example a smartphone, tablet, phablet, laptop or desktop computer, a control system or some other processing device. For example, the interrogator and/or control device could be a smartphone provided with a suitable app that provides a user interface for providing commands to the microcontroller 60 and for accessing the neural probe data received from the communications system 5 and utilising the smartphones communications and camera (optical receiver) capabilities. In another example, the interrogator and/or control device could be a custom device, e.g. based on an FPGA or other suitable processing system.

The communications system 5 comprises an on-board power supply 75. In the example shown in FIGS. 1 to 7, this takes the form of a battery, such as a lithium, lithium-polymer lithium-ion, zinc-air, lithium air or other suitable battery or cell or other power storage device such as a capacitor or supercapacitor. The storage device may be primary or rechargeable. However, although the above are examples of energy storage devices, the on-board power supply 75 could comprise an inductive, resonant and/or radio frequency energy collection device and/or the like so that the communications device 5 and thereby the probe can receive power wirelessly, in use. The on-board power supply may also be or comprise a generator, such as a kinetic or other motion based generator. In this example, the on-board power supply 75 is provided on the second circuit board 15 and power is provided from the on-board power supply 75 to the components on the first circuit board 10 via one or more of the inter-circuit board connectors 40. This also allows power from the on-board power supply 75 to be supplied to the probe 25 via the probe interface 20. Typically, the power from the on-board power supply 75 will be supplied under the control of the microcontroller 60 to provide appropriate power to the signal converter 30 and/or stimulation signals to the probe 25, which may be responsive to commands sent to the microcontroller 60 from the interrogator and/or control device via the receiver 70.

The above arrangement provides a wireless, compact, light communications system or interface for a neural probe that is not overly burdensome or invasive. At the same time, the device is capable of very high data rates and acceptably long operational life between recharges or wired power provision. The communications system is particularly suitable for small animal use, e.g. with mice and other rodents, but is equally beneficial in humans and other larger animals, as it is so compact and light.

The system also allows for real time or almost real time interrogation, analysis and recording, which can be done wirelessly and/or at distance. For example, the communications system or interface may communicate with a device that acts as a relay via optical wireless communications and the relay may connect to wi-fi or some other data network in order to forward the data for remote access or storage.

Method steps of the invention can be performed by one or more programmable processors executing a computer program to perform functions of the invention by operating on input data and generating output. Method steps can also be performed by special purpose logic circuitry, e.g., an FPGA (field programmable gate array) or an ASIC (application-specific integrated circuit) or other customised circuitry. Processors suitable for the execution of a computer program include CPUs and microprocessors, and any one or more processors. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data. Information carriers suitable for embodying computer program instructions and data include all forms of non-volatile memory, including by way of example semiconductor memory devices, e.g. EPROM, EEPROM, and flash memory devices. The processor and the memory can be supplemented by, or incorporated in special purpose logic circuitry.

To provide for interaction with a user, the communication system or interface can be used with a device having a screen, e.g., a CRT (cathode ray tube), plasma, LED (light emitting diode) or LCD (liquid crystal display) monitor, for displaying information to the user and an input device, e.g., a keyboard, touch screen, a mouse, a trackball, and the like by which the user can provide input. Other kinds of devices can be used, for example, feedback provided to the user can be any form of sensory feedback, e.g., visual feedback, auditory feedback, or tactile feedback; and input from the user can be received in any form, including acoustic, speech, or tactile input.

Although particularly beneficial examples are described above, it will be appreciated that these are not limiting. For example, although a particularly beneficial stacked multi-layer communications system is described above, it will be appreciated that it is not essential that the communications system is a stacked multi-layer device, e.g. it could be provided on a single circuit board. Furthermore, although LEDs are used as various light sources, it will be appreciated that other suitable light sources having a suitably fast response time for optical communications could potentially be used, such as laser diodes and/or the like. In addition, although a communications system that is capable of two-way communication (i.e. transmitting the neural probe data and receiving commands), it will be appreciated that the communications system could instead be a one way communications system (e.g. for transmitting the neural probe data only). As such, the above examples are provided only to help understanding of the invention whereas the scope of protection is defined by the claims.

The invention claimed is:

1. An interface for a neural probe, the interface comprising at least one probe interface, an optical communications interface and a processing system, wherein:
    the at least one probe interface is configured to interface with at least one neural probe so as to receive data collected by the probe;
    the processing system is configured to process the data from the at least one probe interface and provide the processed data to the optical communications interface;
    the optical communications interface is an optical wireless communications interface configured to communicate the processed data to remote devices using optical wireless communications; and
    the optical communications interface comprises:
    one or more optical communications light sources operable responsive to the processing system, wherein the processed data is encoded in light signals emitted by the optical communications light sources; and
    a reference or clock communications module, the reference or clock communications module being configured to communicate a clock or reference signal by transmitting the clock or reference signal by optical wireless communication;
    wherein either the reference or clock communications module comprises at least one reference or clock light source configured such that the optical signals emitted by the at least one reference or clock light source are orthogonal or of a different frequency or wavelength to those emitted by the at least one optical communications light source; or the optical communications interface is configured to encode the clock or reference signal in a data stream used to transmit the processed data derived from the data from the at least one probe interface and transmit the data stream using at least one of the one or more optical communications light sources.

2. The interface as claimed in claim 1, wherein the processing system is configured to convert the data received from the neural probe into data for transmission using the optical communications interface.

3. The interface as claimed in claim 1, wherein the optical communications interface is configured to communicate a plurality of different data streams coalesced into a single or combined data or communications stream.

4. The interface of claim 3, wherein one or more or each of the data streams are encoded using Manchester encoding or OFDM, PAM, or PPM signal modulation schemes.

5. The interface as claimed in claim 1, wherein the at least one probe interface is separate to and spaced apart from the optical communication interface and provided on a different side of the communications system to the optical communications interface.

6. The interface as claimed in claim 1, wherein the processing system comprises at least one of: an analogue to digital converter (ADC) for digitizing analogue data carrying signals received from the probe into digital data and an amplifier for amplifying data carrying signals received from the probe.

7. The interface as claimed in claim 6, wherein:
at least one of: the amplifier, the ADC and the at least one neural probe interface are comprised in, on or connected to a first circuit or circuit board; and/or
the processing system comprises at least one processor and one or both of: the at least one processor and the optical communications interface are comprised in, on or connected to a second circuit or circuit board; wherein
the first circuit board and the second circuit board are stacked on different layers or levels; or
the first circuit and second circuit are combined on a single circuit board.

8. The interface as claimed in claim 7, wherein the second circuit is a master and the first circuit is a slave to the second circuit.

9. The interface as claimed in claim 7, wherein at least one of: the first circuit board and the second circuit board are flexible circuit boards.

10. The interface as claimed in claim 6, wherein at least one of the amplifier and the ADC are coupled to one or more registers for temporarily storing data received from the at least one neural probe.

11. The interface as claimed in claim 1; wherein the interface or communications system is formed in a multi-level or layered arrangement comprising different circuits and semiconductor components stacked in different levels or layers.

12. The interface as claimed in claim 1, comprising:
at least one of: a power source and power storage; and
a voltage controller for regulating or controlling the power provided by the power source or power storage to the other components of the communications system.

13. The interface of claim 12, wherein the power source comprises a lithium battery, such as a lithium polymer battery.

14. The interface of claim 12, wherein the power source comprises one or more of: a wireless power supply, an inductive coupling power supply, a radio frequency power supply, or a kinetic or perpetual generator or power supply.

15. The interface as claimed in claim 1, comprising a receiver, the receiver being configured to receive at least one of: commands and other data, wherein:
the commands comprise control commands for controlling the interface or the at least one neural probe; and
the other data comprises stimulation data for provision by the one or more stimulators of the neural probe.

16. A neural probe system comprising:
at least one neural probe;
an optical wireless communications interface; and
a processing system, wherein:
the processing system is configured to process data from the at least one neural probe and
provide the processed data to the optical wireless communications interface; and
the optical wireless communications interface is configured to communicate the processed data to remote devices using optical wireless communications; and,
the optical communications interface comprises:
one or more optical communications light sources operable responsive to the processing system, wherein the processed data is encoded in light signals emitted by the optical communications light sources; and
a reference or clock communications module, the reference or clock communications module being configured to communicate a clock or reference signal by transmitting the clock or reference signal by optical wireless communication;
wherein either
the reference or clock communications module comprises at least one reference or clock light source configured such that the optical signals emitted by the at least one reference or clock light source are orthogonal or of a different frequency or wavelength to those emitted by the at least one optical communications light source; or
the optical communications interface is configured to encode the clock or reference signal in a data stream used to transmit the processed data derived from the data from the at least one probe interface and transmit the data stream using at least one of the one or more optical communications light sources.

17. A method of communicating data from a neural probe using an interface that comprises at least one probe interface, an optical wireless communications interface and a processing system, the method comprising:
receiving data from the neural probe at the at least one probe interface;
processing, by the processing system, the data from the at least one probe interface and provide the processed data to the optical wireless communications interface;
transmitting the data via optical wireless communications using the optical wireless communications interface to a plurality of remote devices using optical wireless communications; and
communicating a clock or reference signal by transmitting the clock or reference signal by optical wireless communication by one of:
communicating the clock or reference signal using optical signals emitted by at least one reference or clock light source, the optical signal emitted by at least one reference or clock light source being orthogonal or of a different frequency or wavelength to those emitted by the at least one optical communications light source; or encoding the clock or reference signal in a data stream used to transmit the processed data derived from the data from the at least one probe interface and transmitting the data stream using at least one of the one or more optical communications light sources.

18. A system comprising a plurality of remote devices, a neural probe, and an interface, wherein: the interface comprises: a probe interface, an optical wireless communications interface and a processing system, wherein:

the probe interface is configured to interface with the neural probe so as to receive data collected by the neural probe;

the processing system is configured to process the data from the at least one probe interface and provide the processed data to the optical wireless communications interface; and the optical wireless communications interface is an optical wireless communications interface configured to communicate the processed data to the plurality of remote devices using optical wireless communication; and the optical communications interface comprises:

one or more optical communications light sources operable responsive to the processing system, wherein the processed data is encoded in light signals emitted by the optical communications light sources; and a reference or clock communications module comprising at least one reference or clock light source, the reference or clock communications module being configured to communicate a clock or reference signal by transmitting the clock or reference signal by optical wireless communication using the reference or clock light source; and wherein either the reference or clock communications module comprises at least one reference or clock light source configured such that the optical signals emitted by the at least one reference or clock light source are orthogonal or of a different frequency or wavelength to those emitted by the at least one optical communications light source; or the optical communications interface is configured to encode the clock or reference signal in a data stream used to transmit the processed data derived from the data from the at least one probe interface and transmit the data stream using at least one of the one or more optical communications light sources; and the plurality of remote devices are configured to receive data collected using the neural probe from the communications system or the neural probe system.

* * * * *